(12) United States Patent
König

(10) Patent No.: US 10,363,011 B2
(45) Date of Patent: Jul. 30, 2019

(54) AUTOMATIC DOSE CONTROL FOR IMAGING MEDICAL DEVICES

(71) Applicant: SIEMENS HEALTHCARE GMBH, Erlangen (DE)

(72) Inventor: Helmut König, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 482 days.

(21) Appl. No.: 15/122,447

(22) PCT Filed: Jul. 7, 2014

(86) PCT No.: PCT/EP2014/064451
§ 371 (c)(1),
(2) Date: Aug. 30, 2016

(87) PCT Pub. No.: WO2015/131962
PCT Pub. Date: Sep. 11, 2015

(65) Prior Publication Data
US 2017/0065243 A1 Mar. 9, 2017

(30) Foreign Application Priority Data
Mar. 5, 2014 (DE) .................. 10 2014 204 028

(51) Int. Cl.
*A61B 6/00* (2006.01)
*G06F 19/00* (2018.01)
(Continued)

(52) U.S. Cl.
CPC .............. *A61B 6/542* (2013.01); *A61B 6/545* (2013.01); *G06F 19/321* (2013.01);
(Continued)

(58) Field of Classification Search
None
See application file for complete search history.

(56) References Cited

U.S. PATENT DOCUMENTS 8,412,544 B2    4/2013  Reiner
9,047,661 B2 *  6/2015  Oda ..................... G06T 7/0012
(Continued)

FOREIGN PATENT DOCUMENTS

WO    WO2012104786 A2    8/2012

OTHER PUBLICATIONS

Digital Imaging and Communications in Medicine (DICOM) Supplement 150: Radiation Dose Summary Information in Radiology Reports, Aug. 2011.
(Continued)

*Primary Examiner* — Thomas R Artman
(74) *Attorney, Agent, or Firm* — Lempia Summerfield Katz LLC

(57) ABSTRACT

The embodiments relate to a method, an analyzer, a radiation dose disturbance system, and a computer program for automatically calculating a target radiation dose of ionizing radiation. In this case, both patient-specific parameters and equipment-specific parameters are taken into account. On a cloud-based data store, reference images are read out that concern the same anatomical target region in which the imminent examination is also intended to be carried out. The anatomical target region is advantageously determined in a manner dependent on the clinical issue. The reference images are evaluated with regard to radiation dose and image quality in order to generate a target radiation dose with a corresponding control command.

20 Claims, 4 Drawing Sheets

(51) Int. Cl.
  *G16H 30/20* (2018.01)
  *G16H 40/63* (2018.01)
  *G16H 20/40* (2018.01)

(52) U.S. Cl.
  CPC ......... *G06F 19/3481* (2013.01); *G16H 30/20* (2018.01); *G16H 40/63* (2018.01); *G16H 20/40* (2018.01)

(56) References Cited

U.S. PATENT DOCUMENTS

| | | | | |
|---|---|---|---|---|
| 9,547,893 | B2* | 1/2017 | Couch | A61B 6/032 |
| 9,792,680 | B2* | 10/2017 | Couch | A61B 6/032 |
| 9,805,464 | B2* | 10/2017 | Couch | A61B 6/032 |
| 2009/0006131 | A1 | 1/2009 | Unger et al. | |
| 2012/0148131 | A1 | 6/2012 | Couch et al. | |
| 2013/0243300 | A1 | 9/2013 | Oda | |
| 2013/0311472 | A1* | 11/2013 | Cohen-Solal | G06F 19/321 |
| | | | | 707/737 |
| 2017/0065243 | A1* | 3/2017 | Konig | G06F 19/3481 |

OTHER PUBLICATIONS

Digital Imaging and Communications in Medicine (DICOM) Supplement 155: Imaging Reports using HL7 Clinical 5 Document Architecture, Jan. 2015.
Digital Imaging and Communications in Medicine (DICOM) Supplement 159: Radiopharmaceutical Radiation Dose Reporting (Dose SR), Nov. 2013.
Digital Imaging and Communications in Medicine (DICOM) Supplement 94: Diagnostic X-Ray Radiation Dose Reporting (Dose SR), Nov. 2005.
Digital Imaging and Communications in Medicine (DICOM) 8 Supplement 127: CT Radiation Dose Reporting (Dose SR), Nov. 2007.
PCT International Search Report and Written Opinion of the International Searching Authority dated Nov. 20, 2014 for corresponding PCT/EP2014/064451, with English Translation.
The Joint Commission—New Release: "Joint Commission Announces New and Revised Diagnostic Imaging Standards: Changes to be implemented in two phases beginning in Jul. 2014," dated Dec. 20, 2013.

* cited by examiner

AUTOMATIC DOSE CONTROL FOR IMAGING MEDICAL DEVICES

The present patent document is a § 371 nationalization of PCT Application Serial Number PCT/EP2014/064451, filed Jul. 7, 2014, designating the United States, which is hereby incorporated by reference, and this patent document also claims the benefit of DE 10 2014 204 028.0, filed Mar. 5, 2014, which is also hereby incorporated by reference.

TECHNICAL FIELD

The present embodiments lie within the fields of medical technology, image processing, and/or electronic controllers.

BACKGROUND

Medical imaging devices, such as, for example, computer tomographs or fluoroscopy devices, use ionizing radiation in order to produce analyzable image data. A fundamental aim is, wherever possible, to expose patients to only such a radiation dose needed to be able to guarantee an adequate image quality. In this context, the radiation dose to be applied and the image quality are in a competing relationship so that the radiation dose is to be determined in each case through consideration of both aspects, which hinders an automatic control of the radiation dose. The dose determination is an important preparatory act in the planning, performance, and/or control of the device in a radiotherapeutic or nuclear medical procedure.

Along with the consideration of how much of a dose reduction is achievable without having to accept interfering losses in image quality, the user is confronted with a multiplicity of examination parameters. Dose measurements are modality-specific measurement methods or estimation methods (e.g., for CT: volume CT dose index (CTDIvol) and dose length product (DLP); for fluoroscopy: dose area product (DAP), kerma area product (KAP), cumulative air kerma (CAK) and entrance surface dose (ESD), etc.). The effects of changes in one or more of these parameters on the image quality and dose often cannot be evaluated in a straightforward manner by the user. Moreover, there are manufacturer-specific parameters, the technical background of which may not be known in detail to the user. Dose optimization is also dependent on the type of imaging examination (e.g., modality employed and type of examination, such as thorax CT and abdomen CT).

Given this complexity, in known methods, radiologists may rely on heuristics and empirical values in the creation of examination protocols. However, the quality assurance measures usable here are unfortunately very restricted. It is thus possible to implement institution-related quality assurance measures whereby, for example, radiologists define institution-related standards for examination protocols based on published studies of leading centers. In addition, the use of ionizing radiation is also controlled in regulatory standards (e.g., the X-ray Ordinance) and by external quality assurance authorities (e.g., a medical authority within the framework of constancy tests). There are also quality assurance programs under the responsibility of medical societies for imaging-controlled interventional procedures (e.g., percutaneous transluminal angioplasty (PTA) of leg arteries) or the inter-institutional comparison of diagnostic examinations (e.g., RSNA Dose Registries for CT examinations in the USA). However, all of these measures either use heuristics, concentrate on specific examination types or the evaluation of the dose (e.g., distribution) on the basis of phantom-based measurements (e.g., model-based dose measurements under controlled conditions that do not take into account the patient constitution and take only restricted account of anatomical structure details).

On this basis, a patient-oriented and patient-specific and case-specific prediction and optimization of examination parameters for dose optimization is possible to a restricted extent only or even not possible at all. Heuristics allow the dose to be influenced within specific orders of magnitudes, e.g., intervals are often indicated for examination parameters or fixed protocols that do not take any account or only take insufficient account of the individual patient constitution, the hardware and software used and the special characteristics of the examination process. An act in quality assurance may include in the avoidance of outliers, e.g., of examinations in which an obviously excessively high dose is used and not in a fine-granularity dose optimization. Due to the high complexity of the relevant parameters, it is not possible for many examination variants simply to refer to publications that describe specifically adapted solutions for the current problem (e.g., complex combination of examination, issues involved, patient constitution, and device type).

In the prior art, a method is known from U.S. Patent Publication No. 2012/0148131 for estimating the radiation applied to a patient radiation during a CT examination on the basis of model-based phantom bodies. However, this procedure has the disadvantage that patient-specific and device-specific dose calculations are not possible. Neither does this publication address the targeted control of an imaging device with respect to the dose values.

On the basis of this prior art, it is the object to provide an automatic dose control system for imaging devices that evaluates the image quality of a plurality of previous examinations. In this context, the previous examinations may be targeted at the same anatomical region. Overall, this may improve the quality of an imaging examination and reduce the radiation intensity for the patient while maintaining an adequate image quality.

SUMMARY AND DESCRIPTION

The scope of the present invention is defined solely by the appended claims and is not affected to any degree by the statements within this summary. The present embodiments may obviate one or more of the drawbacks or limitations in the related art.

The following describes the achievement of the object with respect to the method. Features, advantages, or alternative embodiments may also be transferred to other claimed subject matter and vice versa. In other words, the substantive claims (which are directed for example at a system, an apparatus, or a product) may also be developed with the features described or claimed in connection with the method. In this context, the corresponding functional features of the method are formed by corresponding substantive modules, in particular, by hardware modules.

One aspect relates to a method for automatically calculating target acquisition parameters for the use of ionizing radiation of a region to be irradiated by an imaging device, such as, for example, a computer tomograph, with following method act: the acquisition of patient-specific parameters and/or device-specific parameters; the determination of at least one anatomical target region in which the ionizing radiation is to be applied, wherein the determination is mainly carried out in a manner dependent on the clinical issue and automatically; accessing a data store that is accessible via a network in which a dose-protocol index for a plurality of images with associated radiation dose data or other acquisition parameters (so-called "dose reports") is filed for the selection of at least one reference image that also relates to the at least one anatomical target region determined, approximately corresponds thereto or encompasses the region completely; the automatic evaluation of the at least one reference image selected with respect to the image quality and the acquisition parameters used taking into account the acquired patient-specific and/or device-specific parameters for the calculation of the target acquisition parameters.

The following defines the terminology in more detail.

The imaging device is a medical engineering device for image acquisition. In one embodiment, the image acquisition is effected using ionizing radiation, such as, for example, by a computer tomograph, computer radiography device, X-ray device, tomosynthesis device, and/or fluoroscopy device. In a broader sense, other devices requiring dose determination may also be controlled with the method.

Acquisition parameters are parameters having to be set when the medical device is used.

According to one aspect, radiation dose data is also comprised of the acquisition parameters. The determination of a reconstruction algorithm, the table feed or further technical device parameters are also included. The target acquisition parameters are the acquisition parameters that are used in a future or planned application of ionizing radiation, the dose of which is to be determined and used to control the device.

Hence, the embodiments relate to a method, system, and product and an analyzer for the calculation of a target radiation dose (as a representative of acquisition parameters). This is performed on the basis of the evaluation of ROIs in stored images in that their image quality is determined for the radiation dose used in each case.

Radiation dose data is the total quality of radiation data acquired from past and present applications of ionizing radiation. In this context, the radiation dose recorded per time unit is referred as the dose rate (unit: Sv/s or Sv/h).

The target radiation dose is the radiation dose to be used for a future application of ionizing radiation, the dose of which is to be determined and used to control the device.

The patient-specific parameters are technical measured variables specific to a patient, such as, for example, measured laboratory values, the height, age, or weight of the patient and/or further measured values.

The device-specific parameters are technical measured variables specific to an apparatus or device, such as, for example, the type of examination, the examination protocol, device settings, device manufacturer, and/or further device characteristics.

In one embodiment, the data store is implemented as a cloud system. The data store may be accessed via at least one network interface (e.g., from the internet protocol family or via a SOAP protocol by web services) by electronic or computer-based units (which may also be implemented as a modality client or a part thereof). The data store may be implemented as distributed and distributed on different physical data stores.

The evaluation of the at least one reference image selected with respect to the image quality and the radiation dose used or the acquisition parameters used is performed automatically. The evaluation is performed by taking into account acquired patient-specific and/or device-specific parameters for the calculation of the target radiation dose or the target acquisition parameters.

The dose-protocol index is a specific data structure that may be created in a preprocessing phase. The dose-protocol index may include the units: (1) metadata including a medical indication of a clinical issue, type of procedure, type of modality, medical data; (2) dose-relevant parameters including modality-type-specific, device-specific, in particular hardware-specific, data records including data on the detector type with serial numbers etc. In addition, the device-specific data records may also include software specifics, such as the names and the identification of at least one reconstruction algorithm used and the version thereof and further algorithms (e.g., including imaging processing algorithms, etc.); (3) references to modality protocols (e.g., identification of the examination protocol used to search in the dose-protocol index for the imminent device measurement).

The term "dose-relevant parameters" designates parameters that influence the determination of the dose. According to one aspect, the dose-relevant parameters are also device-specific and hence modality-specific. For example, the following may be taken into account for a computer tomograph: pitch, slice collimation, effective slice thickness, rotation time, tube-current time, current-time product per slice or rotation, tube voltage and/or further values, depending upon the application.

These dose-relevant parameters are used in combination with the aforementioned metadata, details of the clinical indication (e.g., clinical issue), type of procedure, type of modality, patient data, diagnostic data, further medical data, e.g., the severity of the disease, etc., in order automatically to calculate the dose for controlling the imminent examination. The above data is in principle used with all modalities that use fluorescent radiation. Here, express reference is made to the fact that the present embodiments are not restricted to computed tomography and may also be used to control other modalities with respect to the dose determination.

An additional complication is the fact that the calculation of an optimum as possible radiation dose is a complex problem necessitating the consideration of further influential factors. These include in particular parameters relating to the patient (e.g., height, weight, severity of the disease, etc.). For example, it is known that obese patients may need a higher radiation dose than patients of normal weight. It is also necessary to take into account the respective imaging device (for example, the following are relevant for a CT device: pitch, slice collimation, effective slice thickness, rotation time, tube current, current-time product per slice or rotation, tube voltage, etc.)

In summary: the following are provided: an analyzer as an electronic module, a computer program or a computer program product and a system with which the radiation dose for imaging examinations in which ionizing radiation is used may be optimized. Unlike the state of the art, no phantom-based measurements are used in this context. Previous phantom-based measurements known in the state of the art are frequently based on model calculations under controlled conditions that do not take account of the current patient constitution and only take account of the details of the anatomical structures of the patient and/or the respective imaging device to a limited degree. In addition, dose determination is a complex problem, which to date has been expressed manually in examination protocols that were also evaluated quasi manually prior to imminent examinations. This procedure has been found to be disadvantageous since this manual procedure only enables restricted parameters to be taken into account for the dose determination. It is a basic principle of radiology that the lowest possible radiation dose may be used for the patient without having to accept interfering losses in image quality (e.g., ALARA principle: as low as reasonably achievable). The embodiments are directly based on this basic principle and evaluates the image quality of previous images for the dose optimization. The previous images are stored in the data store together with dose information. These images may be stored in the dose-protocol index. Hence, in addition to the actual image data, the dose-protocol index also contains radiation dose data in the form of so-called dose reports. However, not all the available images are evaluated, only those relevant for the imminent examination. Hence, the images for evaluation are selected from the set of images that are in principle available. The selection is based on the technical parameters for the imminent examination. In particular, the evaluation is based on the respective clinical issue. An indication may be used to determine the relevant anatomical structure in each case (e.g., it is also possible to select a plurality of relevant anatomical structures) automatically by a corresponding algorithm. Here, the term "anatomical structure" may be understood as being synonymous with the term "anatomical target region" and is intended to designate the respective region of the body to be examined. Examples of clinical issues or examination indications are inter alia "subarachnoid bleeding", which is an indication for computed tomography of the skull, while the indication "clarification of diffuse abdominal pain" is an indication for computed tomography of the abdomen with the administration of an intravenous contrast medium. It is optionally also possible to take account of further relevant diagnoses, such as, for example, also the severity thereof, for example in the case of pulmonary fibrosis. To remain with the aforementioned example with the indication for the clarification of diffuse abdominal pain: it is possible automatically to derive that computed tomography of the abdomen may be carried for which the dose is to be optimized or calculated. To this end, the reference images evaluated also relate to the abdomen. The anatomical target region was determined in the preceding method act, in this case the abdomen. Now, all reference images from the data store relating to the same anatomical target region (e.g., the abdomen) are automatically collected and evaluated. This means there is an evaluation of all the reference images that completely or partially encompass the abdomen or, in addition to the abdomen, also encompass further surrounding body structures. It is possible to configure which of the aforementioned alternatives are to be implemented.

In the following method act, the image quality of all selected reference images is evaluated and supplied to an evaluation algorithm together with the radiation dose used in each case. In addition, the evaluation algorithm also takes into account the patient-specific parameters acquired in the method act and the device-specific parameters with respect to the technical aspects of the imaging device, the settings thereof, the protocol used etc.

According to one aspect, the evaluation algorithm is based on ready-provided, selectable, and/or variable quantitative quality measures.

The quality measures are based on the measurement of a signal/noise ratio (S/N ratio) of image signals of the at least one reference image. According to one embodiment, this may be entropy-based. It is also possible to use further statistical methods, such as, for example, the determination of the variance or the standard deviation of the pixel values or voxel values, autocorrelation methods or the processing of a noise power spectrum.

According to one embodiment, the evaluation of the image quality of the at least one reference image may be based on a delimitation algorithm. The function of the delimitation algorithm is automatically to analyze how adequately a respective anatomical structure (e.g., tumor tissue, bone structure, heart, etc.) may be delimited from surrounding structures (e.g., anatomical structures or tissue) in the reference image.

The delimitation algorithm may include the following method acts: the automatic detection of a respective anatomical structure in the reference image and the automatic segmentation of the detected anatomical structure.

The delimitation algorithm is based on the evaluation of blur.

In addition, it is still also possible to determine the quality of the segmentation manually.

There is an automatic evaluation of noise and blur for the relevant anatomical structures in each case, which may also be designated regions of interest (ROI). Unlike the case with phantom-based examinations of the image quality, the evaluation is restricted, namely only on the basis of the relevant structures to be examined subsequently and is hence case-specific and patient-oriented. This advantageously enables the technical effect to be obtained in that it is possible to achieve a significant reduction in the data volume to be evaluated and transmitted in that only selected regions in specific (e.g., relevant for the imminent examination) images are evaluated.

The analysis of blur is ROI-based. To this end, the pixel values or voxel values of the boundary region of the respective ROI (e.g., it is also possible for a plurality of ROI regions to be evaluated or a plurality of anatomical target regions) are compared with those of the boundary region of the background or of adjacent ROIs using neighborhood functions. To this end, for example, it is possible to use automated algorithms that evaluate a so-called 8 neighborhood of two-dimensional image data. This procedure permits a selective search for the highest-quality and case-specific dose optimizations with respect to the available image quality. If desired, it is also possible to take account of relevant diagnoses and degrees of severity (e.g., by accessing standardized terminologies and codes in so-called order messages or radiation dose data or dose reports).

In this context, the image noise is, for example, calculated as the standard deviation of the pixel values or voxel values of a region of interest (ROI). In other words, in addition to delimitability (e.g., blur), the automatic evaluation of the noise or signal/noise ratio is the second independent quality measure that is also only evaluated on a ROI basis.

According to one aspect, the images stored in the data store originate from different patients and/or from different imaging devices (e.g., possibly different manufacturers) and/or from different anatomical regions. This has the advantage that it is possible to provide the largest possible total cohort for the dose optimization. To this end, the method is divided into two sequential processing phases: (1) a preprocessing phase and (2) a dose-determination phase.

In the preprocessing phase, all the image data acquired with different modalities are stored in the data store together with their associated and assigned dose reports in each case.

In the dose-determination or optimization phase, the data stored in the data store is then evaluated by the analyzer prior to the imminent examination in order to determine the optimum acquisition parameters for the imminent imaging examination. The evaluation result may also be stored in a separate data structure. It is also possible for the result of the evaluation (evaluation result) to be stored in the dose-protocol index so that it is again available and usable for subsequent examinations for the determination of the acquisition parameters for the imminent imaging examination. In other words, with each image acquisition, the total cohort of the available reference images, which are automatically stored in the data store together with the associated dose data, increases.

The data store may be organized as distributed and/or implemented as a cloud system. It may be accessible via corresponding interfaces (e.g., RESTful Services such as supported via the HTTP protocol). This enables the system to be embodied very flexibly.

With the automatic evaluation of the at least one reference image, in addition to the patient-specific parameters and/or the device-specific parameters, further metadata is taken into account, including (depending upon the embodiment) the type of procedure, the clinical indication, medical data, details of the severity, diagnostic data, weight data, height data, age data for the patient, modality data, device data (relating to the device's hardware and/or software), and further technical device parameters.

In one embodiment, the anatomical target region is determined automatically. Hence, the user does not have to enter a specific anatomical target region (e.g., heart, knee, liver etc.), instead it is sufficient for a clinical issue or indication to be entered or read-in from other databases (e.g., from medical records). The clinical issue or indication is used to determine the relevant anatomical target structures on the basis of regulations. The clinical issue is analyzed automatically by reference to a semantic encoding system with standardized terminology. This enables it to be provided that uniform semantics and controlled terminology are used. It is also possible to take account of regulative standardization specifications relating to protection from ionizing radiation and dose documentation. These may, for example, be derived from the Euratom Directive (Council Directive 97/43/Euratom). It is also possible to refer to further international standards.

According to a further aspect, the anatomical target region is automatically determined in that a DICOM (DICOM: Digital Imaging and Communications in Medicine) header is read-out and/or an automatic detection algorithm is used.

The at least one reference image is selected in that a selection algorithm is used to determine the reference image or reference images from the set of images stored in the data store. In this context, the reference images (e.g., a plurality of reference images) are determined in that an automatic analysis is performed to see whether the anatomical target region determined in each case is partially or completely contained or encompassed in the reference image. Hence, the anatomical target region in the image and reference image corresponds. This has the advantage that the dose optimization may be determined on the basis of reference images that correspond anatomically and clinically and hence is significantly more accurate and more case-specific than previous optimization methods.

According to a further aspect, the selection algorithm may include an image processing algorithm. The image processing algorithm may be used to estimate the noise. To this end, the signal/noise ratio and/or the blur may be evaluated. The image processing algorithm may be used cumulatively or alternatively to select specific regions from the selected images that are relevant for the imminent examination (e.g., the heart in an upper body CT for an imminent heart examination). This advantageously enables the calculation only to be carried out with relevant data records and hence with a much lower data volume.

A further way of achieving the object includes an analyzer (e.g., synonymously designated a dose analyzer) for automatically calculating a target radiation dose or target acquisition parameters of ionizing radiation of a region to be irradiated by an imaging device. The analyzer includes: (1) a parameter acquisition interface, which is intended to acquire patient-specific parameters and/or device-specific parameters; (2) a target region determining unit, which is intended to determine at least one anatomical target region in which the ionizing radiation is to be applied; (3) a network interface for accessing a cloud-based data store, in which a plurality of images with assigned radiation dose data or dose reports are stored and which is intended for the selection of at least one reference image that also relates to the at least one anatomical target region determined, approximately corresponds thereto or encompasses the region completely; and (4) an evaluation unit intended for the automatic evaluation of the at least one reference image selected with respect to the image quality and the radiation dose or acquisition parameters used taking into account the patient-specific and/or device-specific parameters for the calculation of the target radiation dose or the target acquisition parameters.

A further aspect relates to a radiation-dose control system for the automatic calculation or optimization of a target radiation dose of ionizing radiation of a region to be irradiated with: an imaging device, an analyzer and a cloud-based data store, wherein a dose control unit of the imaging device is controlled by an evaluation result of the analyzer.

The above-described embodiments of the method may also be embodied as a computer program product with a computer program, wherein the computer is prompted to carry out the above-described method when the computer program is executed on the computer or on a processor of the computer.

An alternative way of achieving the object also includes a computer program with a computer program code for carrying all the method acts of the claimed or above-described method when the computer program is executed on the computer. In this context, the computer program may also be stored on a machine-readable storage medium.

An alternative way of achieving the object provides a storage medium intended for storing the above-described computer-implemented method and may be read by a computer.

It is also within the scope of the embodiments that not all acts of the method mandatorily are carried out on one and the same computer. Certain acts may also be carried out on different computers. It is also optionally possible to vary the sequence of the method steps.

It is also possible for individual segments of the above-described method to be executed in one marketable unit and the remaining components in another marketable unit—so-to-speak as a distributed system.

BRIEF DESCRIPTION OF THE DRAWINGS

The following detailed description of the figures discusses exemplary embodiments, which should not be understood as restrictive, together with their features and further advantages with reference to the drawings, which show.

Figure 1:
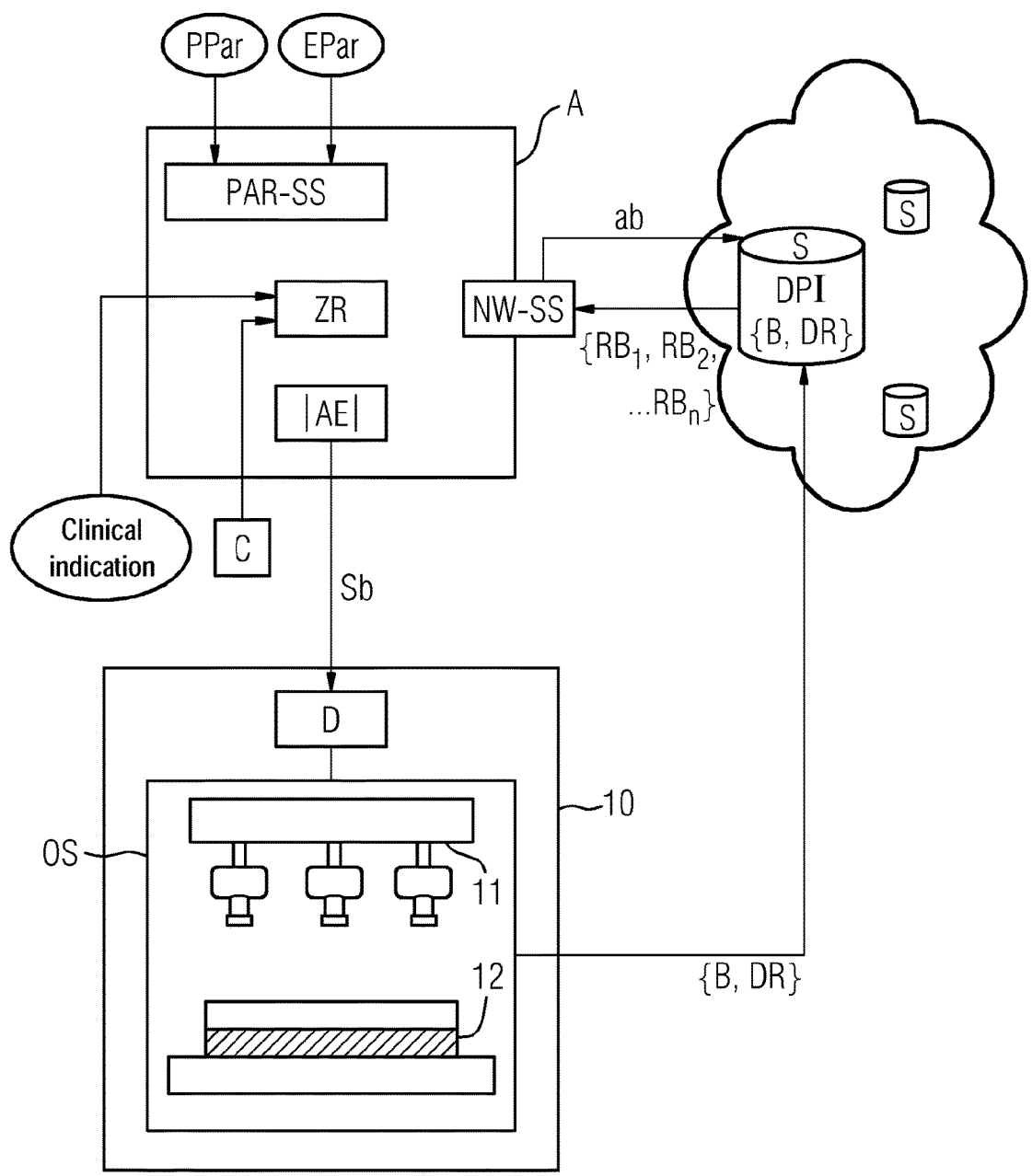
FIG. 1 depicts an overview of a radiation dose control system with modules in data exchange via one or more networks according to an embodiment.

The following provides more detail with reference to exemplary embodiments and with reference to the figures.

DETAILED DESCRIPTION

The embodiments relate to a method, an analyzer A, a radiation dose control system 1, and one or more computer programs or computer program products for calculating and/or optimizing the radiation dose for imaging examinations in which ionizing radiation is used. The object is to generate one or more control commands sb in order to control the imaging device 10 (e.g., the computer tomograph) such that it provides the best possible image quality with the lowest radiation dose in a manner dependent on the respective patient and the clinical issue or the examinations to be performed. In this context, the ALARA principle (as low as reasonably achievable) may be employed for the dose. To this end, inter alia patient-specific parameters PPar and device-specific parameters EPar may be taken into account. The patient-specific parameters PPar relate to the patient to be examined and, for example, include medical data and other dose-relevant data (e.g., weight and height) for the patient. The device-specific parameters EPar are parameters specific to the imaging device 10. This may involve device-dependent parameters, which identify the device's hardware and/or software, are specific to the type of modality and/or refer to a modality protocol to be implemented. If the examination is to be performed with a computed tomography device, the modality-specific parameters also include the pitch, the slice collimation, an effective slice thickness, the rotation time, the tube current, the tube current-time product, etc. During the calculation of the radiation dose, both the patient-specific parameters PPar and the device-specific parameters EPar are taken into account automatically and without further user interaction.

A further feature may be seen in the fact that, in addition to the above-named data records, the current clinical issue in each case is also taken into account. The subsequent calculation in the analyzer A is performed on the basis of the respective clinical issue or the indication. In this context, it is possible to use an encoding system C in order to provide uniform semantics and terminology.

A further feature is characterized in that available and existing images that are stored in a data store S are evaluated. The evaluation is performed with respect to the image quality. However, the images are not arbitrary images, instead there is a targeted selection of images stored in the data store S with respect to the examination to be performed. In other words, corresponding reference images are sought and evaluated with respect to the image quality and possibly further features in order to enable the calculation of a radiation dose that is optimized as greatly as possible for the imminent examination. In this context, the term "corresponding images" means that a selection algorithm is applied to the stored images. The selection algorithm is used to filter out from the set of images available those with the reference images that correspond with respect to the anatomical structures depicted with the anatomical target region in which the ionizing radiation is to be applied during the imminent examination. Therefore, if, for example, a skull CT is to be performed (e.g., due to the clinical issue "cerebral tumor present?"), only skull CT images are evaluated with respect to the image quality and the associated radiation dose in order to be able information for the imminent skull CT examination. In other words, within volume data records, those images are selected that include specific target regions (ROIs) depicting relevant anatomical structures. Hence, the selection may take place in two stages: first, the selection of the relevant images (including the ROI) and, secondly, the selection of the image regions in the images determined as relevant. This may achieve a further reduction in the data volume.

Hence, the method may employ a very large number of previous images for the calculation, which are evaluated with respect to the image quality and the respective radiation dose. On the other hand, the calculation may be performed specifically for the imminent examination in each case. It is further provided that greater account is taken of the previous images including the corresponding patient-specific parameters PPar and corresponding device-specific parameters EPar in order to be able to provide the greatest possible correspondence between the reference image and the image to be taken.

It is clear that the effect of changes to individual or several of the aforementioned influential factors during the determination of the image quality and the dose in a quasi-manual procedure is not able to provide an optimum result without further computer-based support since the problem is too complex. Therefore, previous dose optimization procedures according to the state of the art are inadequate since they are based on heuristics and empirical values that only cover the current specific case in a rudimentary and deficient manner. In particular, such methods are not able to take account of the patient-specific parameters PPar and the current situation of the device with the device-specific parameters EPar. The present embodiments overcome these disadvantages.

FIG. 1 is an overview of a radiation dose control system 1 with a plurality of modules. The core component is the analyzer A, which is depicted as a central element. The analyzer A includes a parameter acquisition interface PAR-SS, which is intended to acquire the patient-specific parameters PPar and/or the device-specific parameters EPar.

The analyzer A also includes a target region determining unit ZR, which is intended to determine at least one anatomical target region in which the ionizing radiation is to be applied. The anatomical target region is also the anatomical body structure that is to be depicted during the imminent examination for which the dose is to be determined.

The analyzer A also includes a network interface NW-SS for accessing a cloud-based data store S, which is depicted on the right-hand side in FIG. 1. The data store S may be embodied as a central memory or as a distributed system and include a plurality of storage instances. In FIG. 1, this is intended to be represented by the plurality of instances of the data store S. A plurality of images is stored in the data store S together with the associated radiation dose data. The radiation dose data may be stored in the form of a dose report in a special data structure, namely in a dose-protocol index DPI. The network interface NW-SS is used to generate a selection command ab and with this access the data store S, in particular the dose-protocol index DPI. The selection command ab includes an identification of the anatomical target region for the imminent examination. On the selection command ab, the reference images RB to be read out of data store S are those corresponding to the anatomical target region. In response to the selection command ab, the data store S returns a set of reference images RB back to the network interface NW-SS. These reference images RB are evaluated by an evaluation unit AE, which may also be a component of the analyzer (as depicted in FIG. 1). However, it is also possible in an alternative embodiment for the evaluation unit AE to be embodied as a separate module or to be integrated as an electronic module in the imaging device 10. It is also possible for the above-mentioned individual modules of the analyzer A also to be embodied as distributed and implemented, not in a common electronic device, but distributed on a plurality of different instances.

The evaluation unit AE is used for the automatic selection of the selected reference images RB. There may be only one reference image RB, if only one reference image RB corresponds to the target region with respect to the anatomical structure. A set of reference images RB may be returned by the data store S in order to calculate the reference images RB with respect to the image quality and the radiation dose used in each case taking into account the patient-specific parameters PPar and/or device-specific parameters EPar acquired. When the evaluation unit AE has determined a target radiation dose, a control command sb may be generated and forwarded to a dose control unit D. The dose control unit D may be a component of the imaging device 10. The imaging device 10 may include one or more radiation sources 11 and a detector 12. As indicated in FIG. 1, the imaging device 10 may also include a plurality of units. These units are explained in more detail below with reference to FIG. 2.

Figure 2:
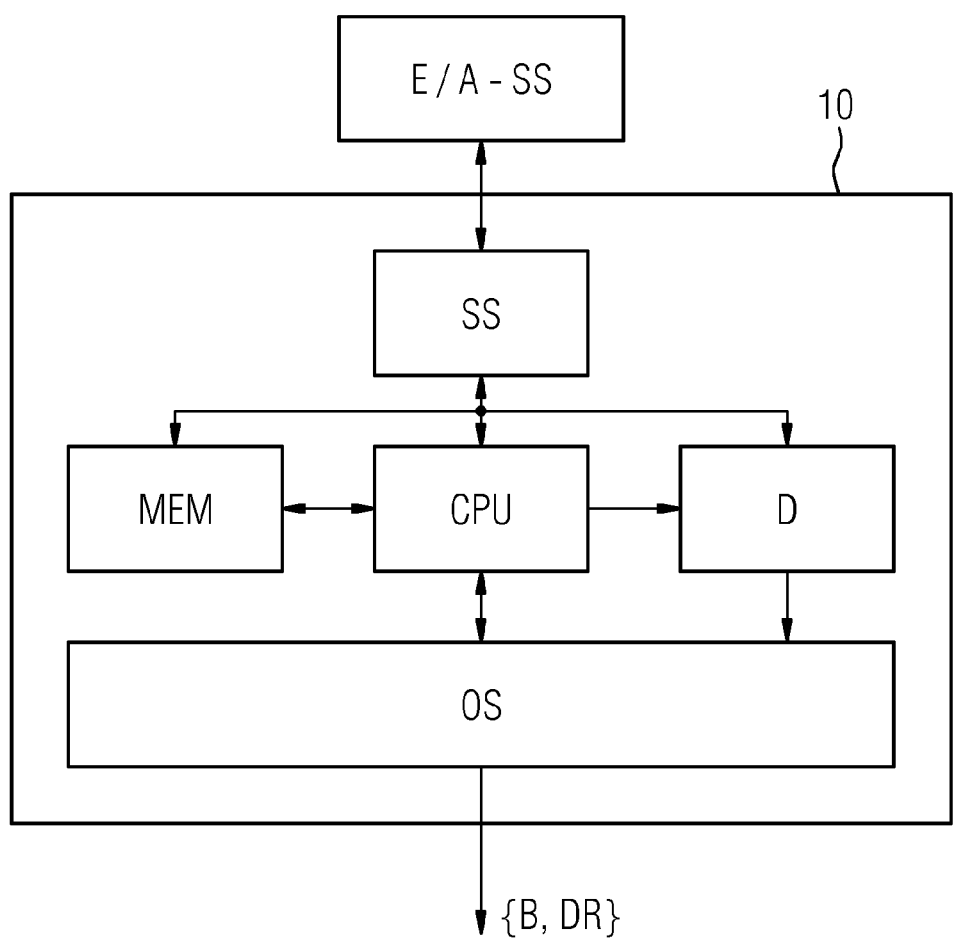
FIG. 2 depicts an overview of a computer tomograph as an imaging device with corresponding interfaces according to an embodiment.

FIG. 2 is an overview of an imaging device 10, which may, for example, be embodied as a computer tomograph with further interfaces. For example, an input/output interface E/A-SS may be provided in order to receive and output input and output data. The imaging device 10 also includes an internal interface SS, a central processing unit CPU, one or more memories MEM, and a dose control unit D, which is intended to control the optical system OS. The optical system OS includes the radiation source 11 and the detector 12. The optical System OS is intended to acquire and output image data B and output this data with the associated (radiation) dose data in the form of a dose report DR. This may take place in the form of a data tuple, which, as depicted in FIG. 1, is forwarded by the imaging device 10 via corresponding interfaces to the cloud-based data store S for storage.

Figure 3:
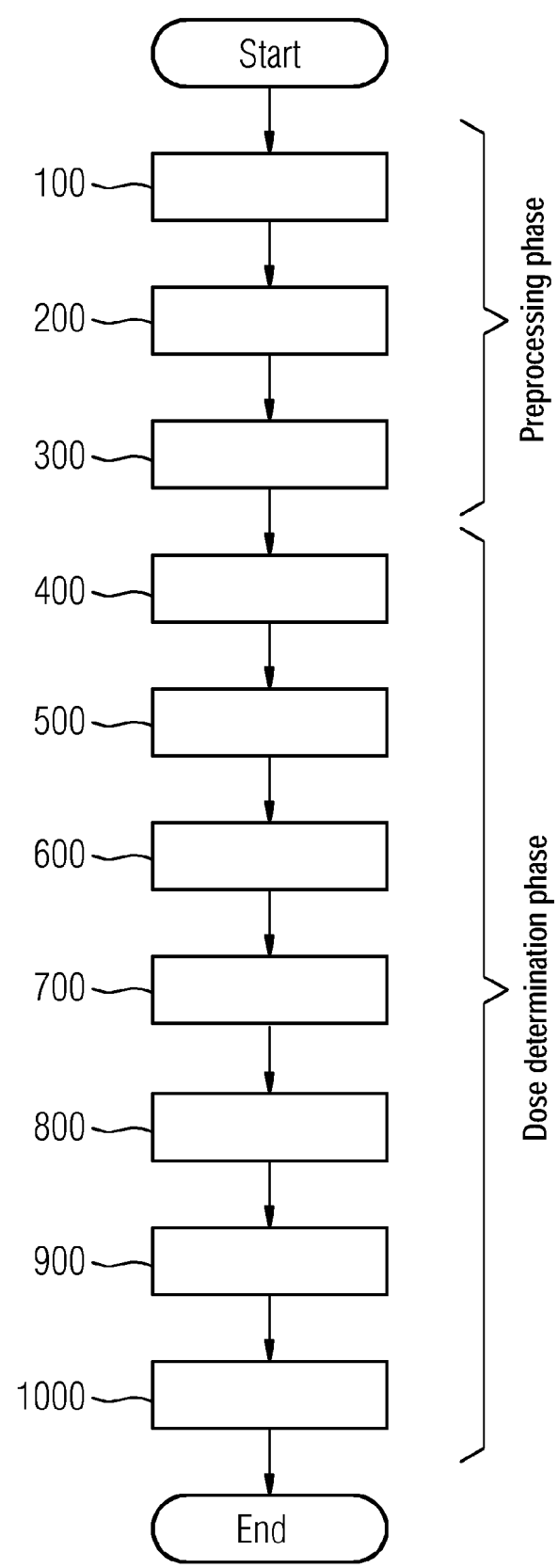
FIG. 3 depicts a flow diagram according to an embodiment of the method.

The following describes the method in more detail according to an embodiment with reference to FIG. 3.

After the method is started, in act 100, the image data B is acquired by the imaging device 10.

Act 200 entails the acquisition of the dose-relevant parameters that may be stored and forwarded in the form of a dose report DR.

Act 300 entails the storage of the image data D in the data store S together with the associated dose report data.

Acts 100 to 300 may be described as a preprocessing phase that temporally precedes the actual dose-determination phase and may be decoupled from the course of the dose-determination phase. The preprocessing phase is used to provide a satisfactory totality of image data that may then be used to select the acquisition parameters for optimizing the dose with the best possible image quality (e.g., determination of the target radiation dose).

The actual dose-determination phase is performed in acts 400 to 1000, which are explained in more detail below. Acts 400 entails the acquisition of device-specific parameters EPar.

Act 500 entails the acquisition of patient-specific parameters PPar.

It is also possible to change the sequence of the individual method acts. In this case, it is also possible initially to acquire the device-specific parameters EPar.

Act 600 entails the automatic the determination of the anatomical target region in which the ionizing radiation is to be applied during the imminent examination.

Act 700 entails access to the data store S with the anatomical target region determined for the selection of at least one reference image RB.

Act 800 entails the automatic computer-based selection of at least one reference image RB. As already explained above, a set of reference images RB may be selected and forwarded to the evaluation unit AE of the analyzer A for the calculation.

Act 900 relates to the automatic, computer-based evaluation of the selected reference images RB with respect to their image quality and dose taking into account the technical parameters PPar, EPar acquired for the determination of a target radiation dose.

Act 1000 entails the output of the control command SB to control the imaging device 10 with respect to the acquisition parameters to be used, which are also used to control the dose to be applied.

After this, the method finishes.

Here, advantageous developments provide different branches from the above-mentioned procedure, but these are not shown in FIG. 3 in order to keep it clear and comprehensible. It is, for example, possible to carry out the method repeatedly if the dose may not be determined satisfactorily. It is also possible to repeat the dose-determination phase from act 400 if further parameters may be determined or parameters have changed.

Figure 4:
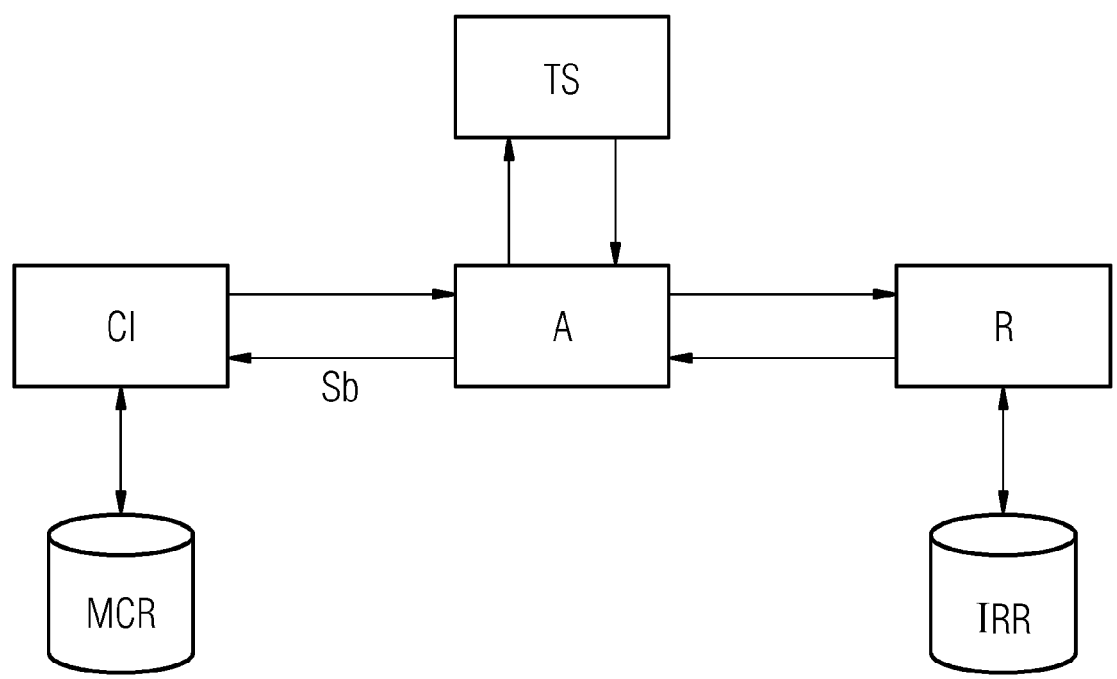
FIG. 4 depicts a schematic view of an analyzer according to an embodiment with further units.

FIG. 4 is an overview of the use and communication of different computer-based units, in particular in the situation at the client Cl or the modality workplace prior to an imminent examination or optionally also decoupled from an imminent current examination. The method may also be used if the use of dose protocols on a modality is to be checked within the context of a quality assurance measure. Hence, FIG. 4 relates to the search for suitable or optimized dose protocols for imminent imaging examinations. The analyzer A carries out an automatic analysis of the image data of reference images with a quality check with respect to noise and blur. Here, the analysis is only performed in the relevant anatomical regions (e.g., in the anatomical target region determined). In this context, it is optionally possible to use a terminology service, which in FIG. 4 is identified with the reference TS. The terminology service TS is used to perform an analysis at semantic level and in particular to analyze semantic relationships between procedure type, modality type and other code values. Subsequently, the dose protocol index DPI is compiled—this contains information on examination protocols with respect to dose optimization and in this context also references the associated image data B and the associated dose reports DR. In this context, the respective dose protocols are modality-specific. Here, as already mentioned, in the case of CT examinations, CT protocols with information on pitch, slice collimation, slice thickness, tube current, tube current-time product, etc., are to be taken into account in the analyzer A. Clients, (e.g., modality clients Cl), may request the dose protocol information prior to immediately imminent examinations via the analyzer A. In this context, information on the type of procedure, indication, type of modality, patient data, and optionally further parameters (e.g., diagnosis, severity) may be taken into account. The results returned to the client Cl are the protocols with the lowest image noise (noise) and the highest possible sharpness (e.g., little blur) for a given dose for the relevant anatomical target region in each case. At the client-side, the images belonging to the best protocols may be checked by the user prior to the imminent imaging examination. The user may confirm or reject the automatically generated suggestion by a user input.

As depicted in FIG. 4, the client may communicate with a modality configuration repository MCR. Further configuration-specific settings and the device-specific settings EPar may be stored in the modality configuration memory. The analyzer A also communicates with a registry R, which, in the embodiment, may also be embodied as an instance of the data store S and includes the dose-protocol index DPI. The registry R may communicate with a further repository, namely with the image and report repository IRR.

Further aspects are described again in more detail with reference to FIG. 1.

There is access to a cloud-based data pool, which may be implemented in the form of the data store S and permits the use and analysis of manufacturer-specific image and assigned metadata and dose reports DR. In addition, device-specific parameters EPar are automatically taken into account (such as, for example, the detector type) and the further parameters with respect to the image acquisition for the subsequent image processing act in the form of image processing algorithms. The image processing algorithms are, for example, characterized by different reconstruction algorithms with convolution kernels and statistical post-processing. The data may advantageously be evaluated in anonymized form without indicating the identity of the patient (e.g., PHI information), such as, for example, name, patient ID, address, etc.

In addition, it is also possible to use an encoding system C in order to be able to provide a uniform terminology for the automatic semantic analysis, such as, for example, specific procedure codes (for example, RadLex Playbook). The encoding system C may also include information with respect to codes for clinical issues (for example, based on Snomed terminology). Relevant anatomical structures, (e.g., the anatomical target region), are determined on the basis of rules and in dependence on the type of examination.

The evaluation unit AE of the analyzer A is used for the automatic evaluation of the reference images RB provided. In this context, initially relevant anatomical structures are segmented and with the use of terminologies—with access to the encoding system C—designated in a unique semantic way in order to enable selective evaluations and comparisons with other reference images RB or images (or studies) (e.g., the determination of ROIs—using the example of the lungs: specific lung arteries in the lung tissue). The codes are stored as metadata for the respective images RB or the dose reports DR. In further acts, the semantically uniquely designated anatomical target regions form the basis for the automated evaluation of the image quality oriented toward relevant anatomical structures. Therefore, precedence is given to the image quality of these relevant anatomical structures since it is necessary to be able to evaluate these accurately in order to respond to the current medical issue (indication). Therefore, the clinical issue and the respective parameters PPar, EPar are also included in the evaluation and the generation of the control command SB.

A substantial advantage may be seen in the fact that the dose optimization may be performed at both interdepartmental level and interorganizational level. Hence, the dose optimization may also be provided as a central solution as a total set of images and radiation dose data for different hospitals and clinical devices with access to a broad database.

Cloud-based storage of the data in the data store S enables access to a very large database in order to be able to calculate the dose optimization on the greatest possible basis. It is also possible to set the dose very specifically for the respective application by inputting the respective parameters PPar, EPar.

As depicted in FIG. 1, these parameters PPar, EPar are included in the evaluation. This also enables metadata for the imaging examinations to be taken into account (for example, DICOM attributes: patient's height, patient's weight, patient's gender, etc.). These parameters may be automatically read from the automatically provided data records determined. The DICOM protocol may be used to this end. The data records may be read from the DICOM header. Hence, it may be depicted that specific medical applications result in different dose settings. For example, it is known that it may be necessary to use higher doses with obese patients than with patients of normal weight in order to be able to provide an adequate image quality. In addition, the height of the patient may influence the scanning region or the scanning length. This may also advantageously be taken into account automatically. In addition, it is also possible to form patient groups according to gender, body mass index, or weight classes.

A further aspect may be considered to be a cloud-based solution. Advantageously, SOAP-based messages are provided or so-called RESTful services (e.g., satisfying the REST conditions; REST: representational state transfer, inter alia HTTP-based commands, such as GET, POST, PUT, DELETE) used in order to be able to provide access to cloud-image and report repositories in the data store S. This may provide a very simple exchange with the cloud-based system. After image acquisition, the images and dose reports DR are stored by the modalities or the assigned workstations in the repositories or in the cloud-data store S. The repositories may also be cloud-based.

Express reference is made to the fact that the automatic calculation of the target radiation dose is performed on the basis of phantom-based estimations. The determination is not performed on a model-based basis, but taking into account the specific patient constitution and the specific anatomical structures and the specific device situation.

One important advantage may be seen in the fact that continuous data acquisition may also entail the provision of a continuous analysis with respect to the optimized dose and similarly of quality control. A feedback loop is provided between the patient examination with the image acquisition on the one hand and the dose determination on the other. It may be automatically provided that, with each image acquisition, the quality of the dose determination may be automatically increased, since a new data record increases the total set of images provided for evaluation. This means that, in addition, the dose determination or optimization method may also be automatically integrated into existing standards. These are, in particular, based on the DICOM standard and may also be based on precursors such as HL7. It is also possible for the archiving to be performed by PACS (Picture Archiving and Communication System) with further information systems. If the system is implemented on the basis of DICOM, all or selected parameters PPar, EPar may be automatically read out from the DICOM header and analyzed automatically with one command and one operation.

One substantial advantage may be seen in the fact that the image data and the dose reports DR are automatically evaluated and analyzed without the user having to the study them or examine them. The image quality is determined from the noise and the blur in the specifically relevant regions.

The method may advantageously be used for imaging examinations, such as lung cancer screenings, other screenings, or follow-up examinations.

Finally, reference is made to the fact that the description of the invention and the exemplary embodiments may in principle not be understood to be restrictive with respect to a specific physical implementation of the invention. For a person skilled in the art, it is in particular evident that the invention may be implemented partially or completely distributed in software and/or hardware and/or on a plurality of physical products—in this context in particular also computer program products.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for automatically calculating at least one target acquisition parameter to control a radiation dose of ionizing radiation of a region to be irradiated by an imaging device, the method comprising:
   acquiring patient-specific parameters, device-specific parameters, or both the patient-specific parameters and the device-specific parameters;
   determining at least one anatomical target region in which the ionizing radiation is to be applied;
   accessing a data store via a network, wherein a dose-protocol index for a plurality of images is stored in the data store together with associated radiation dose data for selecting at least one reference image that relates to the at least one anatomical target region or completely encompasses the at least one anatomical target region; and
   automatically evaluating the at least one reference image selected with respect to the image quality and the radiation dose used, taking into account the acquired patient-specific and/or the device-specific parameters for calculating the at least one target acquisition parameter, wherein the evaluating of the image quality includes a delimitation algorithm in order to automatically analyze how adequately a respective anatomical structure is configured to be delimited from surrounding structures in the reference image.

2. The method of claim 1, wherein the evaluating of the image quality is performed using ready-provided quality measures, selectable quality measures, variable quality measures, or a combination thereof.

3. The method of claim 2, wherein the ready-provided quality measures, the selectable quality measures, and/or the variable quality measures measure a signal/noise ratio of image signals of the at least one reference image.

4. The method of claim 2, wherein the images stored in the data store originate from different patients, different imaging devices, different anatomical regions, or a combination thereof.

5. The method of claim 4, wherein an evaluation result is stored in the dose-protocol index.

6. The method of claim 5, wherein, during the automatic evaluation of the at least one reference image, further metadata are taken into account in addition to the acquired patient-specific parameters and the device-specific parameters.

7. The method of claim 6, wherein the determining of the at least one anatomical target region comprises automatically analyzing an examination indication responsible for the ionizing radiation to be used and using a semantic encoding system.

8. The method of claim 6, wherein the determining of the at least one anatomical target region comprises reading out a Digital Imaging and Communications in Medicine (DICOM) header, using an automatic detection algorithm, or a combination thereof.

9. The method of claim 1, wherein the delimitation algorithm comprises:
   automatically detecting a respective anatomical structure in the reference image; and
   segmenting the detected anatomical structure.

10. The method of claim 1, wherein the images stored in the data store originate from different patients, different imaging devices, different anatomical regions, or a combination thereof.

11. The method of claim 1, wherein the data store is implemented as a distributed system, as a cloud system, or both as the distributed system and as the cloud system.

12. The method of claim 1, wherein an evaluation result is stored in the dose-protocol index.

13. The method of claim 1, wherein, during the automatic evaluation of the at least one reference image, further metadata are taken into account in addition to the acquired patient-specific parameters and the device-specific parameters.

14. The method of claim 1, wherein the determining of the at least one anatomical target region comprises automatically analyzing an examination indication responsible for the ionizing radiation to be used and using a semantic encoding system.

15. The method of claim 1, wherein the determining of the at least one anatomical target region comprises reading out a Digital Imaging and Communications in Medicine (DICOM) header, using an automatic detection algorithm, or a combination thereof.

16. The method of claim 1, wherein a selection algorithm is used to determine the at least one reference image from a set of images stored in the data store, which relate to the at least one anatomical target region and/or encompass the at least one anatomical target region completely.

17. The method of claim 16, wherein the selection algorithm comprises an image processing algorithm.

18. An analyzer for automatically calculating at least one target acquisition parameter to control an imaging device for use of ionizing radiation of a region to be irradiated, the analyzer comprising:
   a parameter acquisition interface configured to acquire patient-specific parameters, device-specific parameters, or both the patient-specific parameters and the device-specific parameters, a target region determining unit configured to determine at least one anatomical target region in which the ionizing radiation is to be applied, a network interface configured to access a cloud-based data store in which a plurality of images with assigned radiation dose data is stored, and to select at least one reference image that relates to the at least one anatomical target region or encompasses the at least one anatomical target region completely; and an evaluation unit configured to automatically evaluate the at least one reference image selected with respect to the image quality and the radiation dose used, taking into account the acquired patient-specific parameters, the device-specific parameters, or both the patient-specific parameters and the device-specific parameters for calculation of the at least one target acquisition parameter, which includes a delimitation algorithm in order to automatically analyze how adequately a respective anatomical structure is configured to be delimited from surrounding structures in the reference image.

19. A radiation dose control system for automatic calculation of at least one target acquisition parameter to control a target radiation dose of ionizing radiation of a region to be irradiated, the system comprising:

an imaging device;

an analyzer comprising:

a parameter acquisition interface configured to acquire patient-specific parameters, device-specific parameters, or both the patient-specific parameters and the device-specific parameters;

a target region determining unit configured to determine at least one anatomical target region in which the ionizing radiation is to be applied;

a network interface configured to access a cloud-based data store in which a plurality of images with assigned radiation dose data is stored, and to select at least one reference image that relates to the at least one anatomical target region or encompasses the at least one anatomical region completely; and an evaluation unit configured to automatically evaluate the at least one reference image selected with respect to the image quality and the radiation dose used, taking into account the acquired patient-specific parameters, the device-specific parameters, or both the patient-specific parameters and the device-specific parameters for calculation of the at least one target acquisition parameter, which includes a delimitation algorithm in order to automatically analyze how adequately a respective anatomical structure is configured to be delimited from surrounding structures in the reference image; and the cloud-based data store, wherein a dose control unit of the imaging device is controlled by an evaluation result of the analyzer.

20. A computer program product configured to be loaded into a memory of a computer with commands configured to be read by the computer for automatically calculating at least one target acquisition parameter to control a radiation dose of ionizing radiation of a region to be irradiated by an imaging device, wherein the memory and the computer code are configured to cause the imaging device to at least perform:

acquire patient-specific parameters, device-specific parameters, or both the patient-specific parameters and the device-specific parameters;

determine at least one anatomical target region in which the ionizing radiation is to be applied;

access a data store via a network, wherein a dose-protocol index for a plurality of images is stored in the data store together with associated radiation dose data for selecting at least one reference image that relates to the at least one anatomical target region or completely encompasses the at least one anatomical target region; and automatically evaluate the at least one reference image selected with respect to the image quality and the radiation dose used, taking into account the acquired patient-specific and/or the device-specific parameters for calculating the at least one target acquisition parameter, wherein the evaluating of the image quality includes a delimitation algorithm in order to automatically analyze how adequately a respective anatomical structure is configured to be delimited from surrounding structures in the reference image.

* * * * *